United States Patent
Koseoglu et al.

(10) Patent No.: US 11,884,615 B2
(45) Date of Patent: Jan. 30, 2024

(54) **MODIFIED BETA ZEOLITIC (*BEA) CATALYST FOR ISOMERIZATION OF ALKYLATED AROMATICS, AND METHOD FOR ISOMERIZATION OF ALKYLATED AROMATICS**

(71) Applicant: SAUDI ARABIAN OIL COMPANY, Dhahran (SA)

(72) Inventors: Omer Refa Koseoglu, Dhahran (SA); Robert Peter Hodgkins, Dhahramn (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/160,048

(22) Filed: Jan. 27, 2021

(65) Prior Publication Data
US 2022/0234035 A1 Jul. 28, 2022

(51) Int. Cl.
| | | |
|---|---|---|
| *C07C 5/27* | (2006.01) | |
| *B01J 21/06* | (2006.01) | |
| *B01J 29/70* | (2006.01) | |
| *B01J 29/12* | (2006.01) | |
| *B01J 29/14* | (2006.01) | |
| *B01J 37/00* | (2006.01) | |

(52) U.S. Cl.
CPC ........... *C07C 5/2737* (2013.01); *B01J 21/063* (2013.01); *B01J 21/066* (2013.01); *B01J 29/126* (2013.01); *B01J 29/146* (2013.01); *B01J 29/7057* (2013.01); *B01J 37/0009* (2013.01); *C07B 2200/09* (2013.01); *C07C 2521/06* (2013.01); *C07C 2529/12* (2013.01); *C07C 2529/14* (2013.01); *C07C 2529/70* (2013.01)

(58) Field of Classification Search
CPC ........................... B01J 29/7057; C01B 39/085
See application file for complete search history.

(56) References Cited

U.S. PATENT DOCUMENTS

| | | | |
|---|---|---|---|
| 3,308,069 A | | 3/1967 | Wadlinger et al. |
| 4,665,255 A | * | 5/1987 | Chang ................. C01B 35/1009 585/475 |
| 4,892,720 A | | 1/1990 | Skeels et al. |
| 5,684,170 A | | 11/1997 | Saxton et al. |
| 8,183,172 B2 | | 5/2012 | Guillon et al. |
| 9,475,737 B2 | | 10/2016 | Khanmamedova et al. |
| 10,266,416 B2 | | 4/2019 | Kegnaes et al. |
| 10,696,608 B2 | | 6/2020 | Detjen et al. |
| 10,941,354 B1 | | 3/2021 | Hodgkins et al. |
| 2002/0082460 A1 | * | 6/2002 | Verduijn ................. C07C 2/864 585/475 |
| 2008/0293989 A1 | * | 11/2008 | Khanmamedova ...... B01J 29/86 585/500 |

FOREIGN PATENT DOCUMENTS

EP 0272862 A2 6/1988

OTHER PUBLICATIONS

"*BEA framework Type" IZA Database of Zeolite Structures copyright 2017, retrieved Oct. 7, 2022. rcsr.fos.su.se/IZA-SC/framework.php?STC=BEA (Year: 2022).*
Bhavana Rakshe, Veda Ramaswamy, and A. V. Ramaswamy—"Acidity and m-xylene isomerization activity of large pore, zirconium-containing alumino-silicate with BEA structure," Journal of Catalysis, vol. 188, pp. 252-260 (1999).
Z. V. Rahbari, M. Khosravan, A. N. Kharat—"Dealumination of mordenite zeolite and its catalytic performance evaluation in m-xylene isomerization reaction," Bulletin of the Chemical Society of Ethiopia, vol. 31/ Issue 2, pp. 281-289 (2017).
Zi et al. "Effect of dealumination defects on the properties of zeolite Y." Applied Catalysis 56.1 (1989): 83-94.

* cited by examiner

*Primary Examiner* — In Suk C Bullock
*Assistant Examiner* — Alyssa L Cepluch
(74) *Attorney, Agent, or Firm* — Leason Ellis LLP

(57) ABSTRACT

The present invention relates to a catalyst for isomerization of alkylated aromatics such as mixed xylenes, using xylene isomerization catalyst particles including post-framework modified *BEA zeolite in which zirconium atoms and/or hafnium atoms, optionally in combination with titanium atoms, form a part of a framework of a beta-type zeolite.

20 Claims, No Drawings

MODIFIED BETA ZEOLITIC (*BEA) CATALYST FOR ISOMERIZATION OF ALKYLATED AROMATICS, AND METHOD FOR ISOMERIZATION OF ALKYLATED AROMATICS

RELATED APPLICATIONS

Not applicable.

BACKGROUND

Field of the Invention

The present disclosure relates to a catalyst for isomerization of alkylated aromatics such as mixed xylenes into particular xylene components, including one or more of para-xylene, ortho-xylene or meta-xylene, and a process for isomerization of alkylated aromatics.

Description of Related Art

Xylenes are particularly important aromatic products for the world market. Therefore, the growing demand for para-xylene has driven expansions of production capacities and the creation of new petrochemical plants. The para-xylene is used as a raw material for many petrochemical products such as purified terephthalic acids.

It is known in the petroleum refining and petrochemical industry to isomerize alkylated aromatics from one or more sources in a refinery into more desirable isomers. In a petrochemical complex, xylenes are recovered by separation of reformate in an aromatic recovery complex. For example, xylene isomerization processes are used to maximize the recovery of a particular xylene isomer from a mixture of C8 aromatic isomers, para-xylene, ortho-xylene, meta-xylene, and ethylbenzene or commonly called "mixed xylenes." The xylene isomerization process is often applied to para-xylene recovery. In certain operations xylene isomerization can be used to maximize the recovery of ortho-xylene or meta-xylene. In the case of para-xylene recovery, a mixed xylene feed is charged to a para-xylene separation unit where the para-xylene isomer is preferentially separated, for instance in an adsorption column. Raffinate from the para-xylene separation unit, substantially free of para-xylene, is passed to a xylene isomerization unit to convert said raffinate to an equilibrium mixture of xylenes including para-xylene. Ortho-xylene and meta-xylene are catalytically isomerized over an acidic catalyst, including zeolitic catalysts, to form para-xylenes. The xylene isomerization unit reestablishes an equilibrium distribution of xylene isomers by producing para-xylene from ortho- and meta-isomers. The effluent from the xylene isomerization unit is recycled back to the xylene adsorption unit for recovery of additional para-xylene. In this manner, the ortho-and meta-isomers are recycled to extinction.

There are generally two different types of reactions that occur in a xylene isomerization reactor. There are isomerization reactions, whereby ethyl-benzenes are converted to xylenes, and whereby and ortho-xylene and meta-xylene are converted to para-xylene. In addition, there are dealkylation reactions, whereby the alkyl group is cleaved from an aromatic ring, such as conversion of ethyl benzene to benzene.

Various catalyst materials have been used for xylene isomerization process. In certain arrangements, acidic catalyst systems are used, while in others, dual functionality catalysts are used. Acidic characteristics promote xylene isomerization and naphthene isomerization for ethylbenzene conversion. Various types of zeolites have been proposed and are in use commercially.

Given the importance of preparing select isomers from mixed alkylated aromatics, it is not surprising that there is a substantial literature on xylene isomerization.

U.S. Pat. No. 4,892,720 to Skeels et al. teaches crystalline zeolitic aluminosilicates of various types including zeolite beta, having at least some of its original framework aluminum atoms replaced by titanium and/or iron.

U.S. Pat. No. 9,475,737 to Khanmamedova et al. teaches non-acidic germanium zeolite having platinum and at least one other active metal thereon for various hydrocarbon conversion processes.

U.S. Pat. No. 8,183,172 to Guillon et al.—teaches a combination of EUO zeolite and other zeolites in an isomerization process.

U.S. Pat. No. 10,696,608 to Detjen et al. teaches xylene isomerization using an alkylation catalyst comprising a molecular sieve including beta zeolite framework.

Catalytic hydrocracking and xylene isomerization are different in purpose and products. In hydrocracking large molecules are broken ("cracked") into smaller ones. While isomerization reactions may occur as a side reaction, it is not the objective, and conditions and feedstocks are different. In xylene isomerization reactions the molecules are converted by intermolecular methyl-shift. The inventors wish to draw attention to U.S. patent application Ser. No. 16/589,719 filed Oct. 1, 2019, incorporated by reference in its entirety. The '719 application teaches, inter alia, hydrocracking catalysts and method for making hydrocracking catalysts comprising an active phase metal and a β zeolite of *BEA framework, wherein a portion of aluminum atoms in said *BEA framework have been substituted, in part, by one or more of zirconium, titanium, and hafnium. In these catalysts, the metal (Ti, Zr, and/or Hf), substitutes for part of the aluminum in the aluminum/silica framework, and essentially become part of the framework. Processes for making these catalysts and their use, are all described in the '719 application. Zeolite based catalysts provide sufficient acidity to function in cracking, which are desirable in hydrocracking.

Given the different aims, and reagents, used in isomerization processes and hydrocracking, it is surprising that the active catalytic support material can be modified to become a xylene isomerization catalyst. Yet, this is the subject of the invention, which is elaborated upon in the disclosure which follows.

Despite the many advances in xylene isomerization processes and their catalysts, the industry is constantly seeking improved catalyst materials, particularly those with improved isomerization rates.

SUMMARY OF THE INVENTION

A method for isomerizing an alkylated aromatics feed including a mixed-xylene feed to produce preferred isomers (xylene isomerization) is provided using xylene isomerization catalysts comprising, consisting of, or consisting essentially of, catalyst particles containing an active catalytic material or support material formed of post-framework modified *BEA zeolite material in which a portion of aluminum atoms constituting a zeolite framework thereof is substituted with zirconium atoms and/or hafnium atoms, optionally in combination with titanium atoms. In certain embodiments the alkylated aromatics feed contains ortho-xylene and/or meta-xylene, and in certain embodiments the alkylated aromatics feed contains relatively small amounts of para-xylene, for instance, 0.01-2 wt %.

In certain embodiments the xylene isomerization catalyst used in a xylene isomerization can include the active catalytic material or active support material of post-framework modified *BEA zeolite as the catalytic particles, or as a component of the catalytic particles. The particles containing the post-framework modified *BEA zeolite can be provided alone or in combination other with xylene isomerization catalyst particles effective for isomerization of an alkylated aromatics feed including a mixed-xylene feed. The post-framework modified *BEA zeolite component is used to form active catalytic material or active support material as is known, optionally in composition with an effective amount with an inorganic oxide component, and optionally including an additional active component.

The post-framework modified *BEA zeolite includes framework-substituted zeolite in which a part of aluminum atoms constituting a *BEA zeolite framework thereof that is substituted with zirconium atoms (Zr), hafnium atoms (Hf), zirconium atoms and hafnium atoms (Zr—Hf), zirconium atoms and titanium atoms (Zr—Ti), hafnium atoms and titanium atoms (Hf—Ti), or hafnium atoms, zirconium atoms and titanium atoms (Hf—Zr—Ti). In certain embodiments, the post-framework modified *BEA zeolite contains from 0.1-5.0 wt % Zr, Hf, Zr/Hf, Zr—Ti, Hf—Ti or Hf—Zr—Ti, as calculated as the oxide basis. As shown herein, such catalysts possess high isomerization activity that is effective for production of xylene isomers.

In the isomerization catalytic composition including the post-framework modified *BEA zeolite component used herein, the *BEA zeolite component and/or the post-framework modified *BEA zeolite preferably possesses one or more, and most preferably all, of the following characteristics:

(a) a crystal lattice constant of a=1.260 to 1.270 nm, b=1.260 to 1.270 nm, and c=2.620 to 2.650 nm;

(b) a specific surface area of 400 to 800 m$^2$/g, preferably 500-700 m$^2$/g, and (c) a molar ratio of 10 to 200 (preferably 10-100, and more preferably, 30-70) in terms of SiO$_2$ to Al$_2$O$_3$.

The "specific surface area" referred to supra relates to the modified zeolite itself, as do all of the other properties listed. The zeolite containing catalyst support has a specific surface area of 150-500 or 150-450 m$^2$/g.

Operating conditions for xylene isomerization reactions include, for example: a reaction temperature range of about 230-450° C., a pressure range of about 1-30 bars, and a liquid hourly space velocity range, on a fresh feed basis relative to the total quantity of xylene isomerization catalysts, of about 0.5-26 h$^{-1}$. The xylene isomerization reactions occur in the presence of added hydrogen, or in the absence of added hydrogen. The xylene isomerization reactions occur in the presence of added hydrogen, or in the absence of added hydrogen. In embodiments in which the xylene isomerization reactions occur in the presence of added hydrogen, a hydrogen to mixed-xylenes molar ratio is in the range of about 0.5:1-10:1.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments, and serve to explain principles and operations of the described and claimed aspects and embodiments.

DETAILED DESCRIPTION

The disclosure provides methods for isomerization of alkylated aromatics including mixed xylenes, using a xylene isomerization catalyst including, as an active catalytic material or active support material, of a beta-type (hereafter "*BEA") zeolite that has been framework substituted. In certain embodiments, the framework-substituted zeolite incorporates one or more of zirconium atoms (Zr), hafnium atoms (Hf), zirconium atoms and hafnium atoms (Zr—Hf), zirconium atoms and titanium atoms (Zr—Ti), hafnium atoms and titanium atoms (Hf—Ti), or hafnium atoms, zirconium atoms and titanium atoms (Hf—Zr—Ti), into its framework to form the post-framework modified *BEA zeolite. The post-framework modified *BEA zeolite as the active catalytic material or active support material which is included in the catalyst particles used in the process herein are made, essentially, by using the processes described in U.S. patent application Ser. No. 16/589,719 filed Oct. 1, 2019, incorporated by reference in its entirety above.

Xylene isomerization catalysts in the process herein include the catalyst particles having post-framework modified *BEA zeolite material. These post-framework modified *BEA zeolite catalyst particles include the post-framework modified *BEA zeolite material alone, in combination with other zeolite materials, and/or in combination with an inorganic oxide component (for example, where the materials are coextruded or otherwise combined during the manufacture of the catalyst particles). In certain embodiments, the isomerization catalyst particles comprise the post-framework modified *BEA zeolite material formed as catalyst particles without binder or other zeolite materials. In certain embodiments, the isomerization catalyst particles comprise the post-framework modified *BEA zeolite material and a binder material formed as catalyst particles, wherein the post-framework modified *BEA zeolite material comprises about 2-99, 2-98, 2-80, 2-70, 20-99, 20-98, 20-80 or 20-70 wt % of the catalyst particles, with the remaining mass comprising the binder. In certain embodiments, the isomerization catalyst particles comprise the post-framework modified *BEA zeolite material and another zeolite material formed as catalyst particles, wherein the post-framework modified *BEA zeolite material comprises about 2-99, 2-98, 2-80, 2-70, 20-99, 20-98, 20-80 or 20-70 wt % of the catalyst particles, with the remaining mass comprising the other zeolite material. In certain embodiments, the isomerization catalyst particles comprise the post-framework modified *BEA zeolite material, a binder, and another zeolite material formed as catalyst particles, wherein the post-framework modified *BEA zeolite material comprises about 2-99, 2-98, 2-80, 2-70, 20-99, 20-98, 20-80 or 20-70 wt % of the catalyst particles, with the remaining mass comprising the binder and the other zeolite material.

The post-framework modified *BEA zeolite catalyst particles are used in a xylene isomerization reactor alone or in effective combination with one or more additional catalyst particles that are suitable for xylene isomerization, in certain embodiments particularly to enhance production of para-xylenes. These one or more additional catalyst particles can include one or more zeolitic materials including USY, AEL, AFI, ATO, Beta, ITH, MFI, MRE, MOR, MWW (including MCM-22 and SSZ-25), NES and/or TUN. In embodiments in which post-framework modified *BEA zeolite catalyst particles are used in combination with other xylene isomerization catalyst particles, the content of post-framework modified *BEA zeolite catalyst particles is about 1-100, 1-99, 1-80, 1-70, 2-100, 2-99, 2-80 or 2-70 wt % of the total mass of all xylene isomerization catalyst particles.

In certain embodiments a method for isomerization of alkyl aromatics hydrocarbons having eight or more carbon atoms per molecule in a hydrocarbon feed comprises reacting the hydrocarbon feed in the presence or absence of hydrogen, under isomerizing conditions, and in the presence of an effective amount of an isomerization catalyst composition including a post-framework modified *BEA zeolite catalyst particles, alone or in combination with other catalyst particles effective for isomerization of alkylated aromatics including mixed xylenes. In certain embodiments a method for isomerization of mixed xylenes in a hydrocarbon feed having predominantly ortho-xylene and meta-xylene comprises reacting the hydrocarbon feed in the presence or absence of hydrogen, under isomerizing conditions, and in the presence of an effective amount of post-framework modified *BEA zeolite catalyst particles.

The post-framework modified *BEA zeolite material included in the isomerization catalyst particles as described herein is a *BEA zeolite in which silicon atoms and aluminum atoms form a zeolite framework and in which a part of the aluminum atoms is substituted with Zr, Hf, Zr/Hf, Zr—Ti, Hf—Ti or Hf—Zr—Ti atoms. The post-framework modified *BEA zeolite component of the isomerization catalyst compositions for isomerizing alkylated aromatics including mixed xylenes generally contains Zr, Hf, Zr/Hf, Zr—Ti, Hf—Ti or Hf—Zr—Ti, in an amount of from 0.1-5.0, 0.1-4.0, 0.1-3.0, 0.2-5.0, 0.2-4.0, 0.2-3.0, 0.3-5.0, 0.3-4.0 or 0.3-3.0 wt %, as calculated on their oxide basis (that is, $ZrO_2$, $TiO_2$ and/or $HfO_2$) and as measured relative to the mass of the post-framework modified *BEA zeolite component. In certain embodiments, the amounts of individual materials supplying Zr, Ti, and Hf can be less than 0.1, 0.2 or 0.3 wt %, but when combined, the total is at least 0.1, 0.2 or 0.3 wt %. It is appreciated by a person of skill in the art, that when the framework-substituted zeolite in the catalyst contains the zirconium atoms and the titanium atoms and/or the hafnium atoms described above, a mass ratio (in terms of oxides) of the zirconium atoms to the titanium atoms and/or the hafnium atoms is not specifically be restricted, and any ratio of zirconium or titanium or hafnium that is effective to carry out the isomerization process herein can be used.

In certain embodiments the post-framework modified *BEA zeolite is:

a framework-substituted zeolite in which a part of aluminum atoms forming a zeolite framework is substituted only with zirconium atoms, and is referred to as a "zirconium-substituted zeolite" or "Zr-BEA";

a framework-substituted zeolite in which a part of aluminum atoms forming a zeolite framework is substituted only with hafnium atoms, and is referred to as a "hafnium-substituted zeolite" or "Hf-BEA";

a framework-substituted zeolite in which a part of aluminum atoms forming a zeolite framework is substituted only with zirconium atoms and titanium atoms, and is referred to as a "zirconium-titanium-substituted zeolite" or "Zr—Ti-BEA";

a framework-substituted zeolite in which a part of aluminum atoms forming a zeolite framework is substituted only with hafnium atoms and titanium atoms, and is referred to as a "hafnium-titanium-substituted zeolite" or "Hf—Ti-BEA";

a framework-substituted zeolite in which a part of aluminum atoms forming a zeolite framework is substituted only with zirconium atoms and hafnium atoms, and is referred to as a "zirconium-hafnium-substituted zeolite" or "Zr—Hf-BEA"; and a framework-substituted zeolite in which a part of aluminum atoms forming a zeolite framework is substituted only with zirconium atoms, titanium and hafnium atoms, and is referred to as "zirconium-titanium-hafnium substituted zeolite" or "Zr—Ti—Hf-BEA."

The presence of the Zr, Hf, Zr/Hf, Zr—Ti, Hf—Ti or Hf—Zr—Ti atoms which are substituted for the aluminum atoms in the post-framework modified *BEA zeolite serve as constituents of the framework of the *BEA zeolite. Substitution can be verified by, for example, X-ray fluorescence, high frequency plasma emission spectrometry, atomic absorption spectrometry, ultraviolet-visible-near-infrared spectrophotometry (UV-Vis-NIR), Fourier transform infrared spectroscopy (FT-IR), and/or nuclear magnetic resonance spectrometry (NMR).

Zeolite Component

In certain embodiments, β (beta-type) zeolite of *BEA framework is used as the raw materials for preparing the framework-substituted zeolite catalyst. Beta-type zeolite refers to zeolite having a crystal lattice constant falling in a range of a=1.260 to 1.270 nm, b=1.260 to 1.270 nm, and c=2.620 to 2.650 nm, a specific surface area of 400 to 800 $m^2/g$ and a molar ratio of $SiO_2$ to $Al_2O_3$ of 10 to 200, preferably 10-100, and more preferably 30-70. The beta-type zeolite may be prepared by any method known in the art.

In additional embodiments, the post-framework modified *BEA zeolite material is combined with another zeolitic material and optionally a binder material to form post-framework modified *BEA zeolite xylene isomerization catalyst particles. The other zeolitic material can include but is not limited to mordenite, ZSM-5, ZSM-11, ZSM-12, ZSM-22, ZSM-23, ZSM 35, Y, USY and beta-type (wherein this beta-type zeolitic component is not the same as the post-framework modified *BEA zeolite described herein). For example, these can be (FAU) framework, which includes USY, having a micropore size related to the 12-member ring when viewed along the [111] direction of 7.4×7.4 Å; (MFI) framework, which includes ZSM-5, having a micropore size related to the 10-member rings when viewed along the [100] and [010] directions of 5.5×5.1 Å and 5.6×5.3 Å, respectively; (MEL) framework, which includes ZSM-11, having a micropore size related to the 10-member ring when viewed along the [100] direction of 5.4×5.3 Å; (MTW) framework, which includes ZSM-12, having a micropore size related to the 12-member ring when viewed along the [010] direction of 5.6×6.0 Å; (TON) framework, which includes ZSM-12, having a micropore size related to the 10-member ring when viewed along the [001] direction of 4.6×5.7 Å; (MTT) framework, which includes ZSM-23, having a micropore size related to the 10-member ring when viewed along the [001] direction of 4.5×5.2 Å; (FER) framework, which includes ZSM-35, having a micropore size related to the 10-member ring and 8-member ring when viewed along the [001] and [010] directions of 4.2×5.4 Å and 3.5×4.8 Å, respectively; and (*BEA) framework, which includes zeolite beta polymorph A, having a micropore size related to the 12-member rings when viewed along the [100] and [001] directions of 6.6×6.7 Å and 5.6×5.6 Å, respectively.

Inorganic Oxide Component

In certain embodiments, the post-framework modified *BEA zeolite xylene isomerization catalyst particles are formed of the post-framework modified *BEA zeolite material, optionally one or more other zeolitic materials, and an effective amount of one or more inorganic oxide components. The combination of materials is coextruded or otherwise combined during the manufacture of the catalyst particles.

The inorganic oxide component typically contains a substance serving as a granulating agent or a binder. Usually, a known substance can be used as a granulating agent or binder for the isomerization catalyst herein. As the inorganic oxide, a porous inorganic oxide used in isomerization catalyst compositions in the related art can be used. Examples thereof include alumina, silica, titania, silica-alumina, alumina-titania, alumina-zirconia, alumina-boria, phosphorus-alumina, silica-alumina-boria, phosphorus-alumina-boria, phosphorus-alumina-silica, silica-alumina-titania, and silica-alumina-zirconia. In certain embodiments of the process for isomerization of alkylated aromatics including mixed xylenes as described herein, an inorganic oxide component comprising alumina is used in the isomerization catalyst compositions.

The post-framework modified *BEA zeolite xylene isomerization catalyst particles, containing an inorganic oxide component (optionally with active components), generally have a surface area in the range of about 150-500, 150-450, 200-500, 200-450 or 300-450 m$^2$/g, and a pore volume in the range of about 0.4-0.75, 0.4-0.65, 0.45-0.75 or 0.45-0.65 ml/g. The content of the post-framework modified *BEA zeolite component and the inorganic oxide component of the catalytic compositions used for isomerization of alkylated aromatics including mixed xylenes as described herein are appropriately determined according to the object. For example, the post-framework modified *BEA zeolite xylene isomerization catalyst particles can have a post-framework modified *BEA zeolite content of about 2-100, 2-90, 2-80, 2-70, 20-100, 20-90, 20-80 or 20-70 wt % (where 100% refers to no inorganic oxide component). When plural types of post-framework modified *BEA zeolite materials are used in post-framework modified *BEA zeolite xylene isomerization catalyst particles, they are used preferably in a proportion so that the sum of the different types of post-framework modified *BEA zeolite components is within the ranges herein.

Additional Active Component

In certain optional embodiments, the post-framework modified *BEA zeolite xylene isomerization catalyst particles (including the post-framework modified *BEA zeolite material alone or in combination with another zeolitic material and/or with an inorganic oxide component) also have impregnated therein an additional active component to enhance catalytic activity for isomerization of alkylated aromatics including mixed xylenes, The active component can include one or more metal components known in the art of mixed xylene isomerization, for example, one or more of platinum, palladium or rhenium or combinations thereof can be used as an additional active component. In certain embodiments nickel and/or molybdenum can be used. For ethylbenzene isomerization, platinum is known to provide the aromatics hydrogenation activity. For olefin saturation that is desired for xylene isomerization with ethylbenzene dealkylation, a platinum, palladium, nickel, molybdenum, rhenium or combinations thereof can be used as an additional active component. The additional active component in the case of noble metals is present in an amount from 0-2, 0-1, 0-0.5, 0-0.4, 0.01-2, 0.01-1, 0.01-1, 0.01-0.5, 0.01-0.4, 0.05-2, 0.05-1, 0.05-0.5, 0.05-0.4, 0.1-2, 0.1-1, 0.1-0.5 or 0.1-0.4 wt % in terms of the metal component (metal mass for noble metals) and based on the mass of the catalyst particles. The additional active component in the case of non-noble metals such as nickel and/or molybdenum is present in an amount from 0-40, 0-35, 0-30, 0-10, 0-5, 0-2, 0-1, 0-0.5, 0-0.4, 0.01-40, 0.01-35, 0.01-30, 0.01-10, 0.01-5, 0.01-2, 0.01-1, 0.01-1, 0.01-0.5, 0.01-0.4, 0.05-40, 0.05-35, 0.05-30, 0.05-10, 0.05-5, 0.05-2, 0.05-1, 0.05-0.5, 0.05-0.4, 0.1-40, 0.1-35, 0.1-30, 0.1-10, 0.1-5, 0.1-2, 0.1-1, 0.1-0.5 or 0.1-0.4 wt % in terms of the metal component (metal, oxide or sulfide mass) based on a mass of the catalyst particles.

Several methods may be used to add the active component(s) to the support, including but not limited to immersion (dipping), incipient wetness, and evaporative. In the most commonly used method, a calcined support is immersed in an excess of solution containing active metals or metal compounds. The solution fills the pores and is also adsorbed on the support surface, and excess solution is removed. In another method, impregnation is carried out using incipient wetness by tumbling or spraying the activated support with a volume of solution having a concentration of metal compound tailored to achieve the targeted metal level, equal to or slightly less than the pore volume of the support. The metal-loaded support is then dried and calcined. Metal oxides are formed in the process; the calcination step is also referred to as oxidation. In another method, evaporative impregnation, the support is saturated with water or with acid solution and immersed into the aqueous solution containing the metal compound. That compound subsequently diffuses into the pores of the support through the aqueous phase.

Framework Substitution of *BEA Zeolite

The post-framework modified *BEA zeolite xylene isomerization catalyst particles include the post-framework modified *BEA zeolite material that is framework-modified. "Framework-modified" means that a portion of the aluminum atoms within the USY zeolite framework are substituted with Zr, Hf, Zr/Hf, Zr—Ti, Hf—Ti or Hf—Zr—Ti atoms, as disclosed in U.S. patent application Ser. No. 16/589,719 filed Oct. 1, 2019, incorporated by reference in its entirety above.

In certain embodiments, a post-framework modified *BEA zeolite material is produced by firing a *BEA zeolite having the properties described herein at about 350-700 or 500-700° C. The Beta zeolite with *BEA framework with zirconium and titanium atoms of used herein has a crystal lattice constant falling in a range of a=1.260 to 1.270 nm, b=1.260 to 1.270 nm, and c=2.620 to 2.650 nm, a specific surface area of 400 to 800 m$^2$/g and a molar ratio of $SiO_2$ to $Al_2O_3$ of 10 to 200, preferably 10-100, and more preferably 30-70. A suspension is formed containing the fired *BEA zeolite, the suspension having a liquid/solid mass ratio of about 5-15. An inorganic acid or an organic acid is added so that a pH of the suspension is about <2.0. Subsequently a solution containing a zirconium compound and/or a hafnium compound, and in certain embodiments also a titanium compound, is mixed. The solution is neutralized with, for example, an aqueous ammonia, so that the pH of the mixed solution is about 7.

In the method for producing *BEA zeolite used in the isomerization catalyst composition herein, a calcined *BEA zeolite is suspended in water having a temperature of about 20-40° C. to form a suspension, wherein the liquid/solid mass ratio is generally in the range of about 5:1-15:1, 5:1-12:1, 8:1-15:1 or 8:1-12:1.

In the method for producing the post-framework modified *BEA zeolite herein, the *BEA zeolite which is the raw material is calcined at a temperature of about 500-700, 500-650, 550-700 or 550-650° C. The time of calcining is typically not critical so long as the targeted post-framework modified *BEA zeolite is obtained, for instance, in a range of about 30 minutes to about 10 hours. In certain embodiments calcining occurs in air. If the calcining temperature is lower than about 500° C., the framework substitution tends to be reduced; at calcining temperatures that exceed about 700° C., the specific surface area of the *BEA zeolite can be reduced, and a framework substitution amount is thus reduced.

Next, an inorganic acid or an organic acid is added thereto so that a pH of the suspension described above is controlled to a range of about <2.0, and subsequently a solution containing a zirconium compound and/or a hafnium compound, optionally in combination with a titanium compound, is added and admixed for 3-5 hours. The thus mixed solution is neutralized (for example, to a pH of about 7.0-7.5), and dried (for example, at a temperature of about 80-180° C.), whereby the post-framework modified *BEA zeolite described above can be obtained.

The inorganic acid use can generally be sulfuric acid, nitric acid, hydrochloric acid and the like. In certain embodiments the selected inorganic acid is sulfuric acid or hydrochloric acid. Further, carboxylic acids can suitably be used as the organic acid described above. The quantity of inorganic acid or organic acid is not critical, so long as the pH of the suspension is controlled in the range of about <2.0. For example, a 0.5-to 4.0-fold molar amount, and in certain embodiments a 0.7 to 3.5-fold molar, amount based on an amount of $Al_2O_3$ in the *BEA zeolite, can be used, although these ranges are not critical.

Suitable zirconium compounds described above include one or more of zirconium sulfate, zirconium nitrate, zirconium chloride and the like. In certain embodiments zirconium sulfate and/or zirconium nitrate are selected. The quantity of the zirconium compound added is generally about 0.1-5.0, 0.1-4.0, 0.1-3.0, 0.2-5.0, 0.2-4.0, 0.2-3.0, 0.3-5.0, 0.3-4.0 or 0.3-3.0 wt %, as calculated on their oxide basis (that is, zirconium oxide) and as measured relative to the mass of the post-framework modified USY zeolite component. Addition of the zirconium compound in an amount of less than about 0.1 wt % fails to improve solid acid characteristics of the zeolite. The addition of the zirconium compound in an amount exceeding 5 wt % tends to cause clogging of pores of the zeolite. An aqueous solution of a zirconium compound prepared by dissolving the zirconium compound in water can be used as the zirconium compound.

Suitable hafnium compounds described above include one or more of hafnium chloride, hafnium nitrate, hafnium fluoride, hafnium bromide, hafnium oxalate and the like. In certain embodiments hafnium chloride and/or hafnium nitrate are selected. The quantity of the hafnium compound added is generally about 0.1-5.0, 0.1-4.0, 0.1-3.0, 0.2-5.0, 0.2-4.0, 0.2-3.0, 0.3-5.0, 0.3-4.0 or 0.3-3.0 wt %, as calculated on their oxide basis (that is, hafnium oxide) and as measured relative to the mass of the post-framework modified USY zeolite component. Addition of the hafnium compound in an amount of less than about 0.1 wt % fails to improve solid acid characteristics of the zeolite. The addition of the hafnium compound in an amount exceeding 5 wt % tends to cause clogging of pores of the zeolite. An aqueous solution of a hafnium compound prepared by dissolving the hafnium compound in water can be used as the hafnium compound.

In embodiments in which titanium is also added, suitable titanium compounds include one or more of titanium sulfate, titanium acetate, titanium chloride, titanium nitrate, and titanium lactate. In certain embodiments titanium sulfate and/or titanium acetate are selected. The quantity of the titanium compound added is generally about 0.1-5.0, 0.1-4.0, 0.1-3.0, 0.2-5.0, 0.2-4.0, 0.2-3.0, 0.3-5.0, 0.3-4.0 or 0.3-3.0 wt %, as calculated on their oxide basis (that is, titanium oxide) and as measured relative to the mass of the post-framework modified USY zeolite component. Addition of the titanium compound in an amount of less than about 0.1 wt % fails to improve solid acid characteristics of the zeolite. The addition of the titanium compound in an amount exceeding 5 wt % tends to cause clogging of pores of the zeolite. An aqueous solution of a titanium compound prepared by dissolving the titanium compound in water can be used as the titanium compound.

A pH of the above suspension is controlled to about <2.0 to prevent a precipitate from being generated during mixing of the aqueous solution of the added compounds (the zirconium compound and/or the hafnium compound, optionally in combination with a titanium compound) with a suspension of the *BEA zeolite described above.

Mixing of the aqueous solution of the added compounds with a suspension of the *BEA zeolite is, in certain embodiments, is conducted by gradually adding said aqueous solution to the suspension. After completion of addition of the aqueous solution described above to the suspension, the solution can be mixed by stirring at, for example, room temperature (about 25-35° C.) for about 3-5 hours. Further, after completion of the above-described mixing, the admixed solution is neutralized by adding an alkali compound such as aqueous ammonia and/or the like, so that a pH thereof is controlled to about 7.0-7.5, whereby the post-framework modified *BEA zeolite described herein is be obtained.

In this regard: when only the zirconium compound (or an aqueous solution thereof) is used as the compound (or an aqueous solution thereof) and added to the suspension described above, the post-framework modified *BEA zeolite (Zr-BEA) in which zirconium atoms are substituted for a part of aluminum atoms forming the framework of the *BEA zeolite is formed; when only the hafnium compound (or an aqueous solution thereof) is used, the post-framework modified *BEA zeolite (Hf-BEA) in which hafnium atoms are substituted for a part of aluminum atoms forming the framework of the *BEA zeolite is formed; when the zirconium compound and the titanium compound (or aqueous solutions thereof) are used, the post-framework modified *BEA zeolite in the catalyst (Zr—Ti-BEA) in which zirconium atoms and titanium atoms are substituted for a part of aluminum atoms forming the framework of the *BEA zeolite is formed; when the zirconium compound and the hafnium compound (or aqueous solutions thereof) are used, the post-framework modified *BEA zeolite in the catalyst (Zr—Hf-BEA) in which zirconium atoms and hafnium atoms are substituted for a part of aluminum atoms forming the framework of the *BEA zeolite is formed; when the hafnium compound and the titanium compound (or aqueous solutions thereof) are used, the post-framework modified *BEA zeolite in the catalyst (Hf—Ti-BEA) in which hafnium atoms and titanium atoms are substituted for a part of aluminum atoms forming the framework of the *BEA zeolite is formed; and when the zirconium compound, the titanium compound and the hafnium compound (or aqueous solutions thereof) are used, the post-framework modified *BEA zeolite in the catalyst (Zr—Ti—Hf-BEA) in which zirconium atoms, titanium atoms and hafnium atoms are substituted for a part of aluminum atoms forming the framework of the *BEA zeolite is formed.

The resulting framework-substituted zeolite can be filtered, if desired, washed with water, and dried at about 80-180° C.; the mixture may be quasi-equilibrated with steam, for instance, at a temperature of from about 600-800° C. for about 10-20 hours.

Formation of Catalyst Particles

The post-framework modified *BEA zeolite xylene isomerization catalyst particles are formed using the post-framework modified *BEA zeolite material as a component in known processes for forming catalyst, for example, by mixing the components and forming them into the desired shapes, for example by extruding or otherwise forming particles, as the post-framework modified *BEA zeolite xylene isomerization catalyst particles. The post-framework modified *BEA zeolite material in the catalytic particles services as an active catalytic material or as an active support material. Optionally an additional active component is incorporated as is known in catalyst manufacturing using active support material formed with the post-framework modified *BEA zeolite material alone or in combination with an inorganic oxide component.

Isomerization of Mixed Xylenes using the Herein Catalyst

The xylene isomerization process is used to maximize the recovery of a particular xylene isomer from a mixture of C8 aromatic isomers, para-xylene, ortho-xylene, meta-xylene, and ethylbenzene or commonly called "mixed xylenes." The xylene isomerization process is most often applied to para-xylene recovery, but it can also be used to maximize the recovery of ortho-xylene or meta-xylene. In the case of para-xylene recovery, a mixed xylene feed is charged to a para-xylene separation unit where the para-xylene isomer is preferentially separated. The raffinate from the para-xylene separation unit, almost entirely free of para-xylene, is then sent to the xylene isomerization unit. In certain embodiments feed to the xylene isomerization unit contains about 0-2.0, 0.01-2.0, 0-1.0, 0.01-1.0, 0-0.5 or 0.01-0.5 wt % para-xylene, for instance, due to inefficiencies in para-xylene separation.

The xylene isomerization unit reestablishes an equilibrium distribution of xylene isomers, by creating para-xylene from ortho-and meta-isomers. The effluent from the xylene isomerization unit is then recycled back to the xylene adsorption unit for recovery of additional para-xylene. In this way, the ortho-and meta-isomers are recycled to extinction. As for the catalyst used, there are two different types of catalysts used in the xylene isomerization process. Two reactions are taking place: isomerization of ethyl-benzene to xylenes and ortho and meta-xylenes to para-xylene; and dealkylation ethyl benzene to benzene.

An apparatus for the mixed-xylenes isomerization process in the present disclosure using the post-framework modified *BEA zeolite xylene isomerization catalyst particles is not particularly limited as long as the foregoing reactions are carried out. Various types of apparatuses may be used. In accordance with some embodiments, the process of the present disclosure may be conducted in a fixed-bed reactor, an ebullated-bed or slurry-bed or moving-bed reactors or CSTR or batch type reactors, and the like.

The mixed-xylenes feed used in the processes herein using the post-framework modified *BEA zeolite xylene isomerization catalyst particles include ortho-xylene and meta-xylene, in certain embodiments with very small amounts of para-xylene as discussed above. In some embodiments, the ortho-xylene and meta-xylene feed is obtained from an aromatic recovery complex, which processes aromatic rich feedstreams such as reformate, FCC naphtha, or pyrolysis gasoline.

Since reformate feeds usually contain a very low amount of sulfur, as they are typically subjected to desulfurization prior to reforming such that the resulting gasoline product contains an acceptable level of sulfur for compliance with current sulfur specification. Aromatic streams from other sources such as FCC naphtha and pyrolysis gasoline generally contain higher levels of impurities than reformate and therefore typically require feed pretreatment to remove contaminants, especially nitrogen (N) and sulfur (S) species. Removal of these species can be effectuated by conventional treatments such as fractionation, adsorption and/or hydrotreating/stripping. In some embodiments, the mixed-xylenes, ortho-xylene and meta-xylene, are within a hydrocarbon feed mixture that contains less than about 0.5, 0.05 or 0.005 ppm sulfur.

The process is conducted at conditions suitable for effectuating an ortho-xylene and meta-xylene isomerization reaction. The isomerization reaction can be carried-out in the presence of hydrogen or in the absence of hydrogen. A person of skill in the art can determine process parameter such as temperature and pressure to achieve the desired result.

Operating conditions for xylene isomerization reactions include, for example: a reaction temperature of about 230-450, 230-400, 230-325, 230-300, 230-290, 250-450, 250-400, 250-325, 250-300, 250-290, 300-450, 300-400, 300-350, 300-325, 350-450 or 350-400° C.; a pressure of about 1-30, 5-30, 10-30, 1-20, 5-20, 8-20, 10-20, 1-15, 5-15, 8-15 or 10-15 bars; a liquid hourly space velocity (LHSV), on a fresh feed basis relative to the total quantity of xylene isomerization catalysts, of about 0.5-26, 3-26, 0.5-20, 3-20, 0.5-12, 3-12, 0.5-10, 3-10, 0.5-8 or 3-8 $h^{-1}$; and a hydrogen to mixed-xylenes molar ratio (wherein "0" represents absence of added hydrogen) of about 0:1-10:1, 0:1-3:1, 0.5:1-10:1, 0.5:1-3:1, 0.8:1-10:1 or 0.8:1-3:1. In embodiments of xylene isomerization in which there is no added hydrogen, suitable reaction temperatures can be in the range, for example, of about 230-300, 230-290, 250-450, 250-300 or 250-290° C., with pressure and space velocity as noted above. During the reactions, ortho-xylene and/or meta-xylene molecules are converted to para-xylene molecules so that the isomerized reaction effluents contains an increased concentration of para-xylene relative to the feed, for instance by at least about 1, 1.3, 2, 3, 3.3, or 4.4 wt %.

Source of Mixed Xylenes

The source of the mixed xylenes can vary. In certain embodiments, mixed xylenes can be obtained from a catalytic reformer, where a stream rich in alkylated aromatics is separated from reformer products in an aromatics recovery complex. In other embodiments, other streams rich in alkylated aromatics can be passed to an aromatics recovery complex, for example derived from one or more of pyrolysis gasoline, bio derived oils, plastic pyrolysis derived oils, hydrotreated coker naphtha, FCC naphtha.

Catalytic reformers are used in refineries to produce reformate, which itself is used as an aromatic rich gasoline blending fraction, or is used as feedstock to produce aromatics, also referred to as benzene, toluene, and xylene (BTX). Due to stringent fuel specifications implemented or being implemented worldwide, for example requiring less than 35 volume % (V %) aromatics and less than 1 V % benzene in gasoline, the reformate fraction is further treated to reduce its aromatics content. Treatment options available include benzene hydrogenation and aromatics extraction. In benzene hydrogenation, the reformate is selectively hydrogenated to reduce the benzene content, and the total aromatics content is reduced by blending if needed. In aromatics extraction, the reformate is sent to an aromatic complex to extract the aromatics, such as benzene, toluene and xylenes, which have a premium chemical value, and to produce an aromatics and benzene free gasoline blending component. The aromatic complex also produces a reject stream or bottoms stream that is very heavy (boiling in the range of about 100-350° C.), which is not suitable as a gasoline blending component.

In some catalytic reforming processes, a naphtha stream is first hydrotreated in hydrotreating unit to produce a hydrotreated naphtha stream. A hydrotreating unit operates under suitable conditions of, for instance, temperature, pressure, hydrogen partial pressure, LHSV, and catalyst selection and loading, which are effective to remove at least enough sulfur and nitrogen to meet requisite product specifications. For instance, hydrotreating in conventional naphtha reforming systems generally occurs under relatively mild conditions that are effective to remove sulfur and nitrogen to less than 0.5 ppmw levels. The hydrotreated naphtha stream is reformed in reforming unit to produce a gasoline reformate product stream. In general, the operating conditions for reforming unit include a temperature in the range of from about 400-600, 400-550, 430-600 or 430-550° C.; a pressure in the range of from about 1-50 or 1-20 bars; a LHSV, on a fresh feed basis relative to the reforming catalysts, in the range of from about 0.5-5 or 0.5-2 $h^{-1}$, and a hydrogen to hydrocarbon feed ratio of from 1:1-50:1 or 1:1-30:1 The reformate is typically sent to a gasoline pool to be blended with other gasoline components to meet the required specifications.

A typical gasoline blending pool includes C4 and heavier hydrocarbons having boiling points of less than about 180-205° C. In the catalytic reforming process, paraffins and naphthenes are restructured to produce isomerized paraffins and aromatics of relatively higher octane numbers. Catalytic reforming converts low octane n-paraffins to i-paraffins and naphthenes. Naphthenes are converted to higher octane aromatics. The aromatics are left essentially unchanged or some may be hydrogenated to form naphthenes due to reverse reactions taking place in the presence of hydrogen.

The reactions involved in catalytic reforming are commonly grouped into the four categories of cracking, dehydrocyclization, dehydrogenation and isomerization. A particular hydrocarbon/naphtha feed molecule may undergo more than one category of reaction and/or may form more than one product.

An effective quantity of reforming catalyst is provided. Such catalysts include mono-functional or bi-functional reforming catalysts, which generally contain one or more active metal component of metals or metal compounds (oxides or sulfides) selected from the Periodic Table of the Elements IUPAC Groups 8-10. A bi-functional catalyst has both metal sites and acidic sites. In certain embodiments, the active metal component can include one or more of Pt, Re, Au, Pd, Ge, Ni, Ag, Sn, Ir or halides. The active metal component is typically deposited or otherwise incorporated on a support, such as amorphous alumina, amorphous silica alumina, zeolites, or combinations thereof. In certain embodiments, effective reforming catalysts including IUPAC Group 8 metals of the Periodic Table, including precious metals such as Pt or Pt-alloy active metal components, which are supported on alumina, silica or silica-alumina. The hydrocarbon/naphtha feed composition, the impurities present therein, and the desired products will determine such process parameters as choice of catalyst(s), process type, and the like. Types of chemical reactions can be targeted by a selection of catalyst or operating conditions known to those of ordinary skill in the art to influence both the yield and selectivity of conversion of paraffinic and naphthenic hydrocarbon precursors to particular aromatic hydrocarbon structures.

The hydrocarbon/naphtha feed composition, the impurities present therein, and the desired products determine process parameters including selection of catalyst(s), process type and the like. Types of chemical reactions can be targeted by a selection of catalyst and/or operating conditions to influence both the yield and selectivity of conversion of paraffinic and naphthenic hydrocarbon precursors to particular aromatic hydrocarbon structures.

There are several types of catalytic reforming process configurations that carry out the reforming reactions, and differ mainly regarding regeneration of the reforming catalyst to remove coke formed during reaction. Catalyst regeneration, which involves combusting coke formed on catalyst particles in the presence of oxygen, includes a semi-regenerative process, cyclic regeneration, and continuous regeneration. Semi-regeneration is the simplest configuration, and the entire unit, which can include plural reactors in the series, is shut-down for regeneration of catalyst in all reactors. Cyclic configurations utilize an additional parallel reactor to permit one reactor at a time to be taken off-line for regeneration while the others remain in service in a swing mode of operation. Continuous catalyst regeneration configurations, which are the most complex, provide for essentially uninterrupted operation by catalyst removal, regeneration and replacement. While continuous catalyst regeneration configurations include the ability to increase the severity of the operating conditions due to higher catalyst activity, the associated capital investment is necessarily higher.

The reformate from a catalytic reforming unit is usually sent to an aromatics recovery complex where it undergoes several processing steps in order to recover high value products such as xylenes and benzene, and to convert lower value products such as toluene into higher value products. For example, the aromatics present in the reformate are usually separated into different fractions by carbon number, such as benzene, toluene, xylenes, and ethylbenzene, etc. The C8 fraction is then subjected to a processing scheme to make more high value para-xylene. Para-xylene is usually recovered in high purity from the C8 fraction by separating the para-xylene from the ortho-xylene, meta-xylene, and ethylbenzene using selective adsorption or crystallization.

The ortho-xylene and meta-xylene remaining from the para-xylene separation are isomerized to produce an equilibrium mixture of xylenes. The ethylbenzene is isomerized into xylenes or is dealkylated to benzene and ethane. The para-xylene is then separated from the ortho-xylene and the meta-xylene using adsorption or crystallization and the para-xylene-depleted-stream is recycled to extinction to the isomerization unit and then to the para-xylene recovery unit until all of the ortho-xylene and meta-xylene are converted to para-xylene and recovered. In accordance with an embodiment, the isomerization unit includes an effective amount of an isomerization catalyst composition including the post-framework modified *BEA zeolite.

Toluene is recovered as a separate fraction, and then may be converted into higher value products, for example benzene in addition to or alternative to xylenes. One toluene conversion process involves the disproportionation of toluene to produce additional benzene and xylenes. Another process involves the hydrodealkylation of toluene to produce benzene. Both toluene disproportionation and toluene hydrodealkylation result in the formation of benzene, and in certain embodiments it is desirable that the toluene conversion does not result in the formation of significant quantities of benzene.

EXAMPLES

Example 1

A beta zeolite of *BEA framework, having a silica/alumina ratio ("SAR" hereafter) of 28.5 was used. A total of 51.4 g of this zeolite was suspended in 450 g of deionized water, and heated to 40° C. A total of 14.8 g of $H_2SO_4$ (25 wt %) was added, together with 10.0 g of an aqueous solution of titanium sulfate (equivalent to 5 wt % $TiO_2$). The solution contained 8.48 g deionized water and 1.52 g titanium sulfate (equivalent to 33 wt % $TiO_2$). An additional aqueous zirconium sulfate solution (2.8 g, constituting 18 wt % $ZrO_2$) was added, and the mixture was stirred for 4 hours, then filtered and washed with 1.5 liters of deionized water. This took place at 60° C. The resulting zeolite was dried at 110° C. to yield a framework substituted, Zi—Tr-BEA zeolite.

The *BEA zeolite and framework substituted *BEA zeolite were analyzed, and the results follow in Table 1.

Example 2

Ortho-xylene was isomerized using the framework substituted Zr—Ti-BEA zeolite produced in Example 1. Reactions were carried out in a continuous flow fixed-bed reactor under atmospheric pressure at 260° C., in the absence of hydrogen and in an argon atmosphere over the catalyst at a weighted hourly space velocity of 0.71. Results of the reaction are presented in Table 2.

The method and system of the present invention have been described above; however, modifications will be apparent to those of ordinary skill in the art and the scope of protection for the invention is to be defined by the claims that follow.

TABLE 1

Compositional analysis of zeolite Beta before and after Zr—Ti treatment.

| Zeolite | $SiO_2/Al_2O_3$ ratio mol/mol | $ZrO_2$ % | $TiO_2$ % | Surface Area $m^2/g$ |
|---|---|---|---|---|
| β-Zeolite | 28.5 | — | — | 623 |
| β-Zeolite + Zr—Ti | 53.5 | 0.31 | 0.84 | 614 |

TABLE 2

| Name | Retention time (min) | Wt. % (after 65 min) |
|---|---|---|
| Benzene | 4.64 | 0.02 |
| Toluene | 5.37 | 0.12 |
| m-Xylene | 6.11 | 0.17 |
| p-Xylene | 6.16 | 5.91 |
| o-Xylene | 6.56 | 93.63 |
| 1,3,5-Trimethylbenzene | 7.05 | 0.03 |
| 1,2,4-Trimethylbenzene | 7.45 | 0.11 |
| 1,2,3-Trimethylbenzene | 8.08 | 0.01 |
| Tetramethylbenzenes | 9.40 | 0.00 |

*Retention time is the time of elution using gas chromatography.

The invention claimed is:

1. A process for isomerization of a hydrocarbon feed comprising ortho-xylene and/or meta-xylene comprising contacting the hydrocarbon feed with isomerization catalyst particles containing framework-modified beta-type (*BEA) zeolite in which a portion of aluminum atoms constituting a zeolite framework thereof is substituted with zirconium atoms and/or hafnium atoms, wherein the framework-modified *BEA zeolite has a crystal lattice constant of a=1.260 to 1.270 nm, b=1.260 to 1.270 nm, and c=2.620 to 2.650 nm, a specific surface area of 400 to 800 $m^2/g$, and a molar ratio of $SiO_2$ to $Al_2O_3$ of 10 to 70; and the framework-modified *BEA zeolite being an active catalytic material or active support material;

wherein the ortho-xylene and/or meta-xylene are converted to para-xylene.

2. The process according to claim 1, further wherein a portion of aluminum atoms constituting a zeolite framework of said framework-modified *BEA zeolite is substituted with titanium atoms.

3. The process according to claim 1, wherein said framework-modified *BEA zeolite contains from 0.1 to 5 mass % zirconium and/or hafnium as calculated as the oxide basis.

4. The process according to claim 1, wherein said framework-modified *BEA zeolite contains from 0.1 to 5 mass % zirconium as calculated as the oxide basis.

5. The process according to claim 2, wherein said framework-modified *BEA zeolite contains from 0.1 to 5 mass % zirconium and titanium as calculated as the oxide basis.

6. The process according to claim 1, wherein said isomerization catalyst particles are formed of framework-modified *BEA zeolite and an inorganic oxide material as a binder.

7. The process according to claim 6, wherein said inorganic oxide material is selected from the group consisting of alumina, silica, titania, silica-alumina, alumina-titania, alumina-zirconia, alumina-boria, phosphorus-alumina, silica-alumina-boria, phosphorus-alumina-boria, phosphorus-alumina-silica, silica-alumina-titania, and silica-alumina-zirconia.

8. The process according to claim 6, wherein said framework-modified *BEA zeolite comprises about 2-99 wt % of the isomerization catalyst particles, wherein any remaining mass comprising the inorganic oxide material.

9. The process according to claim 1, wherein said isomerization catalyst particles are formed of framework-modified *BEA zeolite and another zeolite material.

10. The process according to claim 9, wherein said framework-modified *BEA zeolite comprises about 2-99 wt % of the isomerization catalyst particles, with the remaining mass comprising the other zeolite material.

11. The process according to claim 1, wherein said isomerization catalyst particles are formed of framework-modified *BEA zeolite, another zeolite material and an inorganic oxide material as a binder.

12. The process according to claim 1, wherein said framework-modified *BEA zeolite is an active catalytic material support in the absence of an additional active component.

13. The process according to claim 1, wherein said framework-modified *BEA zeolite is an active support material support, and wherein an additional active component is carried on said active support material.

14. The process according to claim 13, wherein said active component is selected from the group of metals consisting of platinum, palladium and rhenium, and wherein said active component is present in an amount from 0.01-2 wt % in terms of the mass of the metal component relative to the mass of the catalyst particles.

15. The process according to claim 13, wherein said active component is selected from the group of metals consisting of nickel and molybdenum, and wherein said active component is present in an amount from 0.01-40 wt % in terms of the mass of the metal component based on the mass of the catalyst particles.

16. The process according to claim 1, wherein contacting the hydrocarbon feed with the isomerization catalyst composition occurs at reaction temperature range of about 230-450° C., a pressure range of about 1-30 bars and a LHSV range, on a fresh feed basis relative to the isomerization catalysts, of about 0.5-26 h$^{-1}$.

17. The process according to claim 16, wherein contacting the hydrocarbon feed with the isomerization catalyst composition occurs in the absence of hydrogen.

18. The process according to claim 16, wherein contacting the hydrocarbon feed with the isomerization catalyst composition occurs in the presence of hydrogen at a hydrogen to mixed-xylenes molar ratio range of about 0.5:1 to 10:1.

19. A process for isomerization of a hydrocarbon feed comprising ortho-xylene and/or meta-xylene into para-xylene, comprising contacting the hydrocarbon feed with isomerization catalyst particles containing framework-modified beta-type (*BEA) zeolite in which a portion of aluminum atoms constituting a zeolite framework thereof is substituted with zirconium atoms and/or hafnium atoms formed by a method comprising the steps of:
   suspending calcined *BEA zeolite in water to form a suspension;
   adding an acid, and a zirconium compound and/or a hafnium compound, to form a mixed solution;
   neutralizing the mixed solution; and
   obtaining the framework-modified beta-type (*BEA) zeolite by filtering and drying;
   wherein the framework-modified *BEA zeolite has a crystal lattice constant of a=1.260 to 1.270 nm, b=1.260 to 1.270 nm, and c=2.620 to 2.650 nm, a specific surface area of 400 to 800 m$^2$/g, and a molar ratio of SiO$_2$ to Al$_2$O$_3$ of 10 to 70; and
   the framework-modified *BEA zeolite being an active catalytic material or active support material.

20. The process as in claim 19, wherein the mixed solution comprises the zirconium compound and a titanium compound, wherein the framework-modified beta-type (*BEA) zeolite comprises a portion of aluminum atoms constituting a zeolite framework thereof substituted with zirconium atoms and titanium atoms, and wherein the framework-modified beta-type (*BEA) zeolite comprises 0.1 to 5 mass % zirconium and titanium as calculated as the oxide basis.

* * * * *